(12) United States Patent
Etienne et al.

(10) Patent No.: US 6,818,892 B1
(45) Date of Patent: Nov. 16, 2004

(54) SYSTEM AND METHOD FOR INFRA-RED DETECTION

(75) Inventors: Steven Etienne, Middlesex (GB); Ian Weaver, Surrey (GB)

(73) Assignee: Spectraprobe Limited, Middlesex (GB)

(*) Notice: Subject to any disclaimer, the term of this patent is extended or adjusted under 35 U.S.C. 154(b) by 0 days.

(21) Appl. No.: 09/958,433

(22) PCT Filed: Apr. 10, 2000

(86) PCT No.: PCT/GB00/01368

§ 371 (c)(1),
(2), (4) Date: Jan. 28, 2002

(87) PCT Pub. No.: WO00/62028

PCT Pub. Date: Oct. 19, 2000

(30) Foreign Application Priority Data

Apr. 9, 1999 (GB) .............................. 9908170

(51) Int. Cl.⁷ ............................................. H01L 21/64
(52) U.S. Cl. .................................................. 250/338.3
(58) Field of Search ........................... 250/338.3, 341.2

(56) References Cited

U.S. PATENT DOCUMENTS

| | | | | |
|---|---|---|---|---|
| 4,383,174 A | * | 5/1983 | Matsumura et al. | 250/338.3 |
| 4,910,402 A | * | 3/1990 | McMillan | 250/341.2 |
| 4,945,240 A | | 7/1990 | Nix et al. | |
| 5,021,662 A | | 6/1991 | Johnson | |
| 5,051,551 A | | 9/1991 | Doyle | |
| 5,193,911 A | | 3/1993 | Nix et al. | |
| 5,569,921 A | * | 10/1996 | Sato et al. | 250/341.2 |
| 5,828,066 A | | 10/1998 | Messerschmidt | |

FOREIGN PATENT DOCUMENTS

| | | |
|---|---|---|
| DE | 195 06 192 A 1 | 7/1995 |
| DE | 44 14 975 A 1 | 11/1995 |
| EP | 0 345 048 A2 | 12/1989 |
| GB | 2 286 041 A | 8/1995 |
| JP | 61097539 | 5/1986 |
| JP | 63129677 | 6/1988 |
| JP | 03123078 | 5/1991 |

OTHER PUBLICATIONS

Application of Pyroelectric Sensor and IR–Chopper with Ferroelectric Liquid Crystal for Human Detection—Junya Kobayashi et al, T.IEE Japan vol. 117–E, No. 3 1997, pp. 132–136.
(Mn,Sb) Doped–PZT/YBa2Cu307—Heterostructure for IR Detector Array—Y.Q.Xu et al, Mat. Res. Symp. Proc. vol. 493—1998 Materials Research Society, pp 481–486.

* cited by examiner

Primary Examiner—Constantine Hannaher
(74) Attorney, Agent, or Firm—Martin Fleit; Paul D. Bianco; Fleit Kain Gibbons Gutman Bongini & Bianco P.L.

(57) ABSTRACT

A thermal detector comprises a rigid, frame-shaped support structure which supports a flexible, thin and substantially planar membrane of pyroelectric material. The major surfaces of the pyroelectric membrane carry electrodes, one of which is a common electrode and the other of which is defined as an array. One detector fabrication method involves preparing layered support structure and membrane components as separate assemblies and securing them together prior to performing finishing process steps. In an alternative method, a layered substrate is used as the foundation of a one-stage technique involving back-etching, and the frame-shaped support structure is created by processing the layered substrate subsequent to the attachment of the membrane thereto.

6 Claims, 14 Drawing Sheets

SYSTEM AND METHOD FOR INFRA-RED DETECTION

TECHNICAL FIELD

The present invention relates to a system and method for analysing a material using infra-red detection. It relates particularly, but not exclusively, to the design and manufacture of an infra-red detector for use in such a system and method.

BACKGROUND ART

Infra-red (IR) radiation is the put of the electromagnetic spectrum that lies between visible light and microwave radiation. The absorption of infra-red radiation by a material gives extremely useful information about the molecular structure of that material. If infra-red radiation is directed through a material some wavelengths will be absorbed by the material and some will be transmitted by the material. Analysis of the resulting absorption spectrum can thus reveal details about the molecular groups present in the material, and can therefore be used to identify the material. This technique is known as infra-red spectroscopy.

Most spectrometers for the infra-red wavelength fall into one of two categories: 1) dispersive or 2) Fourier transform. In a dispersive spectrometer, an optical clement causes light at different wavelengths to be refracted at slightly different angles. Hence by measuring the amount of light at each angle, a spectrum can be obtained. In a Fourier transform spectrometer, an interferometer with a time varying optical path difference causes the intensity of light at different wavelengths to oscillate at slightly different frequencies. By recording these oscillations as a function of time and mathematically performing a Fourier transform on the data, a spectrum is obtained.

In general, instruments that are used to perform infra-red spectroscopy on materials utilise the Fourier transform technique (also known as FTIR), and they also employ a so single detector element. The performance of these instruments is extremely good, but generally they are bulky and not portable. Another disadvantage is that samples are collected and brought to the instrument to be analysed, rather than analysing the sample in situ. A further disadvantage of these instruments is that they are extremely expensive.

An example of such an instrument is manufactured by Mettler Toledo in conjunction with ASI Applied Systems. It consists of a bench mounted FTTR instrument connected via an optical conduit to a small probe that can be immersed into a liquid sample. The price of this instrument is, however, in the region of seventy thousand pounds.

An infra-red spectrometer having multiple IR sources is disclosed In U.S. Pat. No. 5.323,066 (R. G. messerschmidt). The spectrometer has a complex arrangement of mirrors, a spatial light modulator which has deformable mirror elements, and a to controller that deforms the mirror elements in order to obtain the spectra. This arrangement of components is very complex and contains many moving parts.

A method and apparatus for real-time inline material monitoring is described in U.S. Pat. No. 5.021,662 (Texas Instruments). The system includes a infra-red source a diffraction grating, and a set of at least six mirrors which are used to reflect and focus infra-red radiation within the device.

An aim of the present invention is to provide improvements in, or relating to, an infra-red detector, and in particular the use of such a detector in a system for analysing a material using infra-red radiation. Another aim of the present invention is to provide a system that has simpler optics than existing systems, and is therefore cheaper to manufacture. It is a further aim of the present invention that the system is portable, and that in situ analysis of a material is possible.

DISCLOSURE OF INVENTION

Embodiments of the invention provide methods of fabricating thermal detectors as claimed in the claims hereof.

BRIEF DESCRIPTION OF DRAWINGS

A number of embodiments of the invention will now be described by way of example only, with reference to the accompanying FIGS., in which.

DETAILED DESCRIPTION OF PREFERRED EMBODIMENTS

Figure 1:
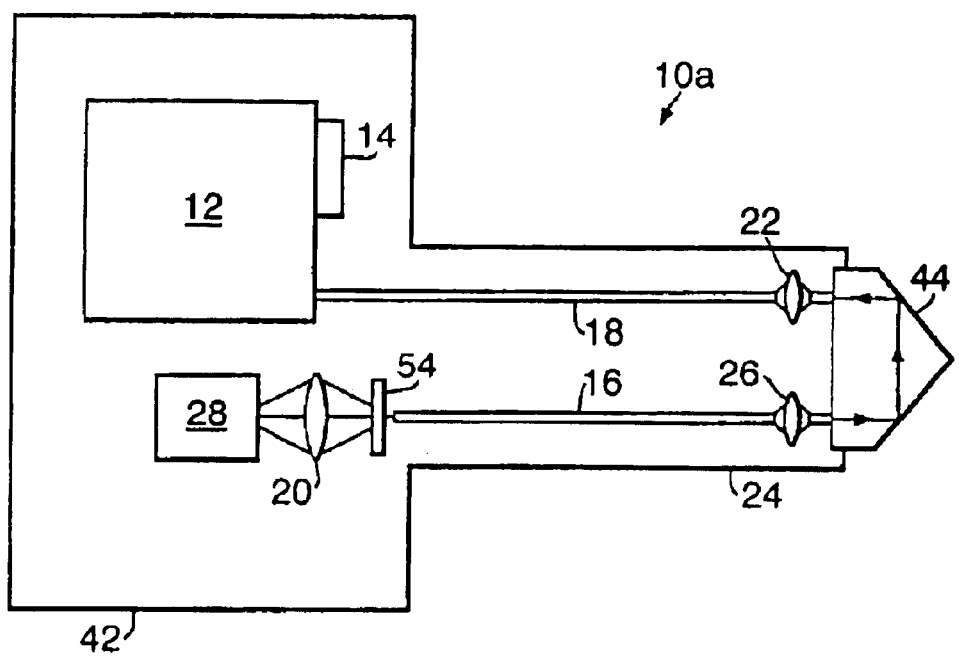
FIG. 1 shows a schematic view of a first modular system for analysing a material.

Referring to FIG. 1, there is shown a schematic view of a first embodiment of a modular system (10) for analysing a liquid. The system (10) comprises a rectangular housing (42) to which an elongated probe (24) is attached, and includes the following parts: a spectrometer (12), an infrared detector (14), first and second optical fiber bundles (16) and (18), first (20) and second (22) converging lenses, collimating lens (26), infra-red source (28), attenuated total reflectance (ATR) element (44) and chopper (54). The probe (24) is the same diameter as a typical pH-sensor, that is, 12mm (or ½ inch) wide. It can be manufactured to be, typically, 360 mm in length so that it may fit existing process machinery. The operation of the system (10) will now be described.

Infra-red radiation is emitted from the source (28) and is directed towards the first converging lens (20). The IR beam (50) is pulsed at a rate of between, for example, 5 to 50 Hz, by the use of the chopper (34) which is placed between the first converging lens (20) and the first optical fiber bundle (16). In this example, the chopper (54) is a resonant optical modulator (i.e. a tuning fork chopper) having crossing paddles that periodically permit the passage of IR radiation, such as manufactured by Electro-Optical Products Corp. A suitable infra-red source (28) for use with the chopper (54) is an efficient low power source such as the LC-IR-12, manufactured by SCITEC Instruments Limited. Alternatively, the IR source (28) may be electrically modulated to (i.e. turned on and off), in which case no chopper is required, and suitable IR sources (238) are the ReflectIR™ and the PulsIR™, manufactured by Ion Optics Inc.

The first converging lens (20) is used to collect light from the IR source (28) and to focus the IR beam (50) onto the end of the first fiber optic bundle (16). The beam of radiation (50) passes along the first fiber optic bundle (16) to the ATR element (44) via collimating lens (26). The collimating lens (26) forms a parallel beam of radiation (50) from the cone-shaped beam which exits from optical fiber bundle (16). The paralel beam of radiation (50) then passes into the ATR element (44) which is located at the end of probe (24).

Figure 3:
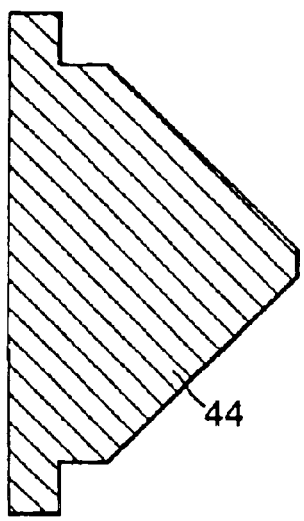
FIG. 3 shows an engineering drawing of a cross-sectional view of an attenuated total reflectance element.
Figure 2:
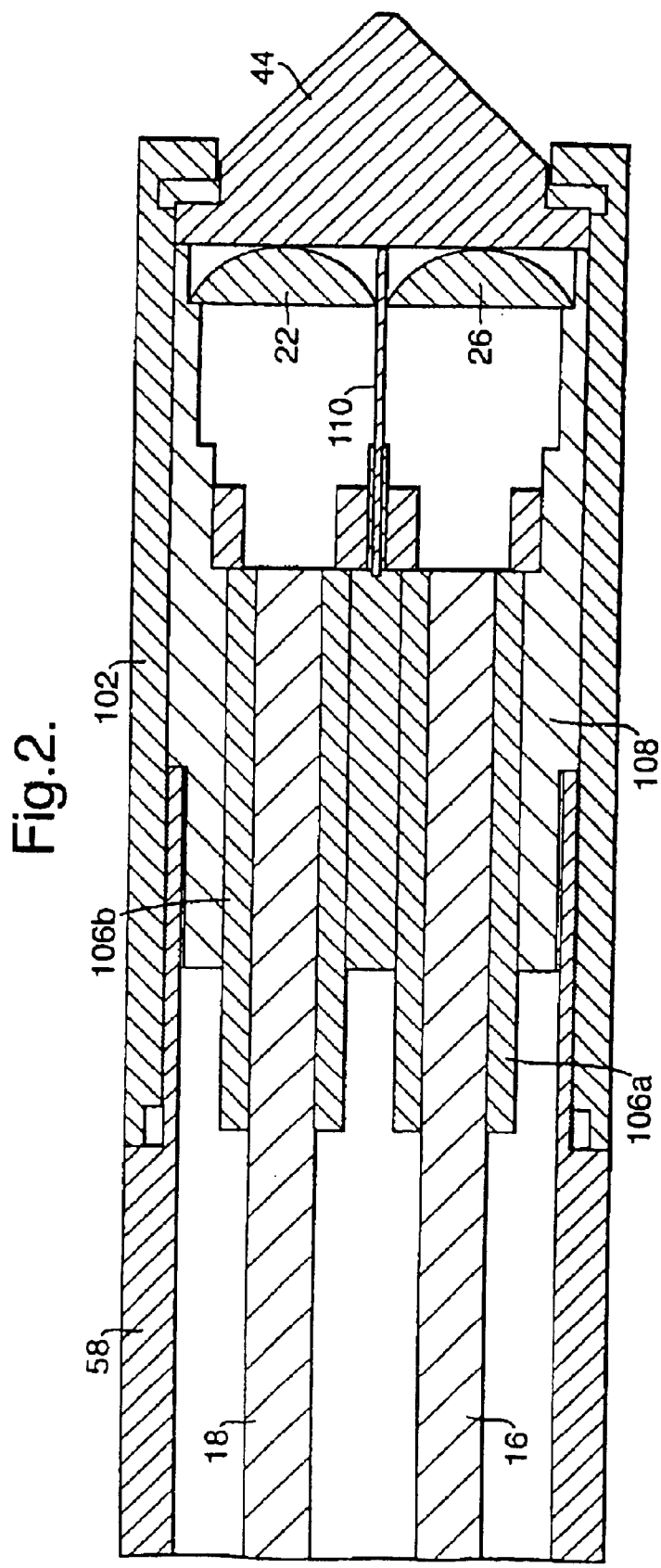
FIG. 2 shows an engineering drawing of a cross-sectional view of a probe.

The probe (24) is formed from an elongated hollow tube of circular cross-section with the ATR element (44) located at its distal end. An engineering drawing of a cross-section of part of the probe is shown in FIG. 2. The ATR element (44) is generally conical and is kept in place by way of a probe end cap (102) which is located at the end of the probe. The ATR element (44) is made from any material that is transparent to the wavelength of interest such as, for example, zinc selenide (which is transparent between 0.6 and 21 micrometers), zinc sulphide or germanium. In order to avoid losses due to reflection of IR at the element (44) surfaces, the base of the element (44) is coated with an anti-reflection coating. A sectional view of the ATR element (44) is shown in FIG. 3.

Figure 4:
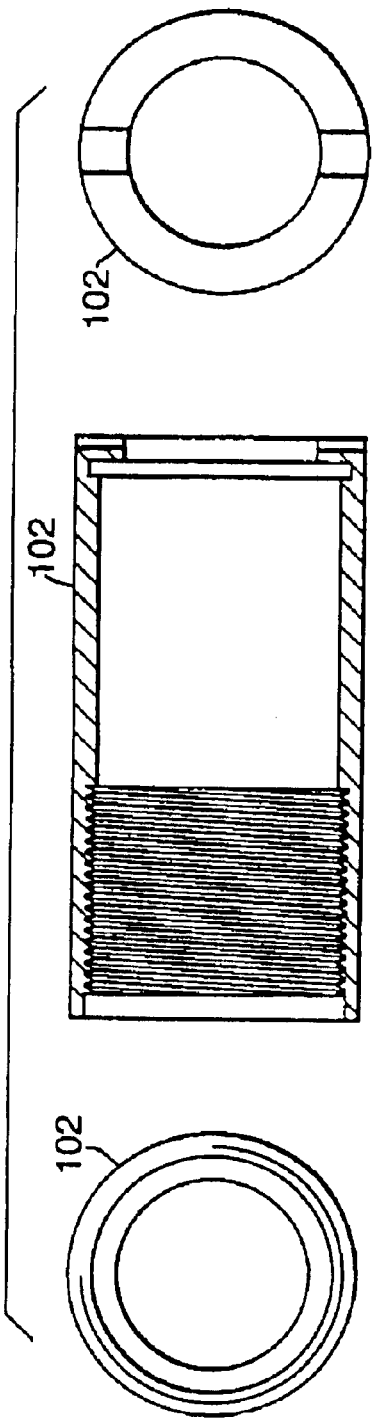
FIG. 4 shows engineering drawings of several views of the probe end cap.
Figure 5:
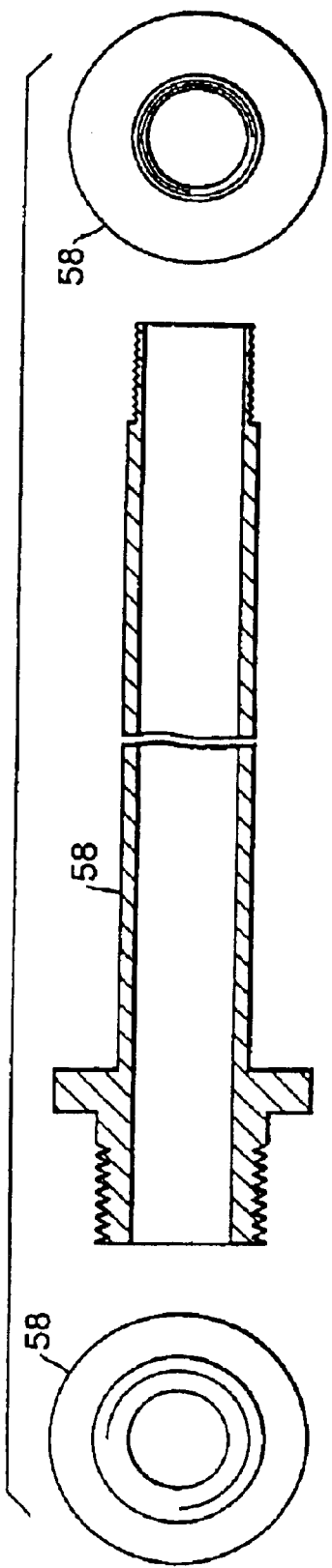
FIG. 5 shows a number of engineering drawings of the body of the probe.

The probe end cap (102) is tubular (of a similar diameter to the probe body) and has a lip (104) formed at its distal end extending radially inwards. Thus the apex of the ATR element (44) protrudes from the end of the probe (24) and so can be placed in contact with the material to be analysed. Sectional views of the probe end cap (102) and the body (58) of the probe are shown in FIGS. 4 and 5, respectively.

Figure 6:
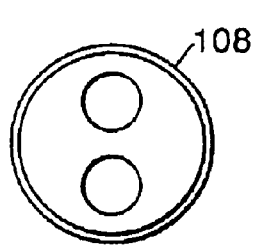
FIG. 6 shows a number of engineering drawings of a lens block and a lens shim.
Figure 6:
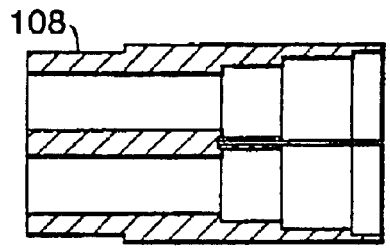
Figure 6:
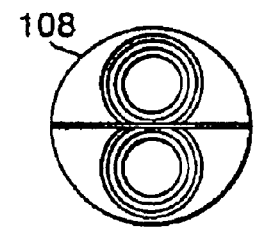
Figure 6:
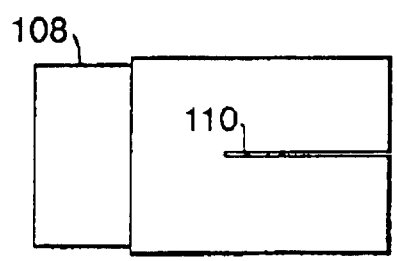

The lenses (26) and (22) shown in FIG. 2 are planar-convex and are positioned at the ends of fiber optic bundles (16) and (18) respectively adjacent the base of the conical ATR element (44). The fiber optic bundles (16) and (18) do not extend fully the length of the probe so that there is a gap (or air space) between the ends of the fiber optic bundles (16) and (18) and the lenses (26) and (22), respectively. The fiber optic bundles (16) and (18) are secured at the distal end of the probe by encasing a short section or the ends of the fibers with ferrules (106a,b). The lenses (26) and (22) are secured in position by portions of lens block material (108) and a central lens shim (110). The lens block material (108) is disposed a) in the spaces between the inner surface of the probe end cup (102) and the ferrules (106a,b), and b) in the space between the ferrules to form a central lens block portion. The central lens shim (110) extends axially from the base of the ATR element (44) to the central lens block portion. FIG. 6 shows an engineering of sectional views of the lens block portions the central lens shim (110).

Figure 7:
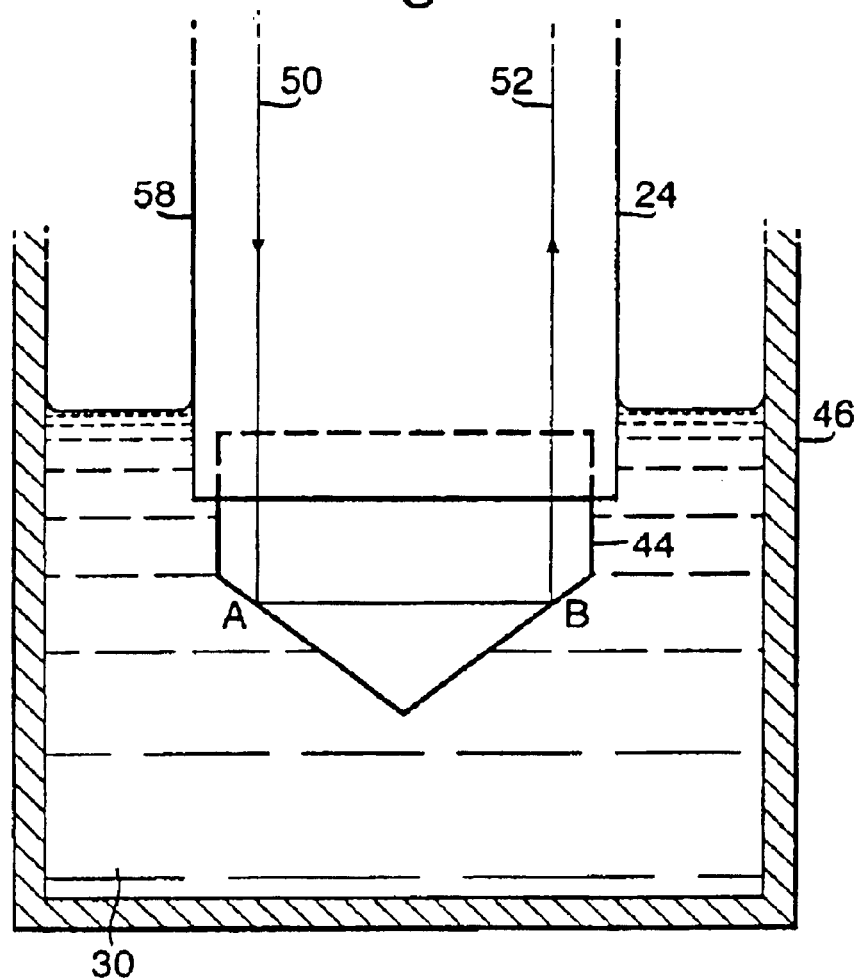
FIG. 7 shows a schematic cross-sectional view of the probe inserted in a liquid sample.
Figure 8:
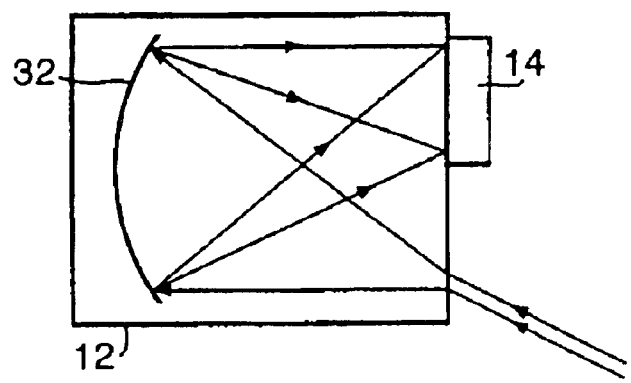
FIG. 8 shows a schematic cross-sectional view of a spectrometer.

The ATR element (44) is conical in shape so that: 1) the IR beam (50) is reflected twice within the ATR element, and 2) the LR beam (52) exiting from the ATR element follows a path parallel to the incoming IR beam (50). This is shown schematically in FIG. 7. When analysing a liquid sample (30), the probe (24) is inserted into the liquid so that the regions A and B of the ATR at which the radiation beam is reflected are completely immersed. The incoming IR beam (30) is reflected by the liquid sample (30) which is to be analysed. The liquid (30) absorbs particular wavelengths of the IR radiation (50) resulting in a modified beam of IR radiation (52) exiting from ATR element (44). The modified MR beam (52) is then focused onto fiber optic connection (18) by the second converging lens (22). The IR beam passes along the probe body (58) via the second fiber optic connection (18) and is then dispersed onto imaging diffraction grating (32) which is contained within the housing (42). The IR beam is then focused onto the detector (14) by the Imaging diffraction grating (32)—shown schematically in FIG. 8.

The fiber optic bundles (16) and (18) are both formed from four optic fibers arranged in an array. A slit is formed in the spectrometer (12) which enables the second fiber optic bundle (18) to pass from the probe (24) into the spectrometer (12). In order for the IR radiation (52) to pass more efficiently from the probe body (24) to the spectrometer (12) the separate optical fibers of the fiber optic bundle (18) at the slit are arranged in a one dimensional array. The optical connections (16,18) can be made of any suitable material that is transmissive to mid-IR radiation such as, for example, silver halide based glass or chalcogenide glass.

The lenses (20,22,26,34,36) used in the system (10) can include zinc selenide, zinc to sulphide, diamond, germanium or other suitable materials. In order to minimise loss when radiation passes through the lenses, they are coated with an anti-reflection coating.

Figure 9:
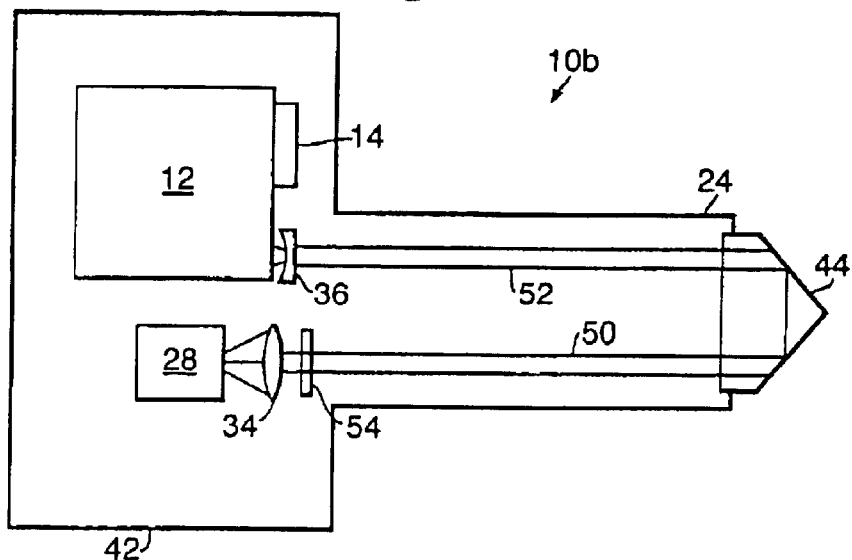
FIG. 9 shows a schematic cross-sectional view of a second modular system for analysing a material.

A further embodiment of the invention is shown in FIG. 9. In this embodiment, instead of fiber optic connections (16) and (13) the beam of IR (50) passes through A dry air/nitrogen atmosphere. The IR beam is directed to and from the material to be analysed by the interior surfaces of the probe (24) which are polished and/or coated with a highly reflective material.

As the infra-red beam (50) does not have to be focused onto the end of an optical connection, the converging lens (20) of the previous embodiment is replaced by a collimating lens (34) which produces a parallel beam (50) of IR radiation. The parallel beam (50) passes through the air/nitrogen atmosphere to the ATR element (44) positioned (as in the first embodiment) at the end of the probe (24) IR beam (50) is reflected by the ATR element (44) to produce a modified beam (52). The modified beam (52) traverses the probe in an opposite (and parallel) direction to the first beam (50) and, on exiting the probe, is focused and dispersed onto diffraction grating (32) by a diverging tens (36). The diffraction grating (32) has between 10 and 40 grooves per mm defined thereon, and is used to focus the beam (52) onto detector (14).

Figure 10:
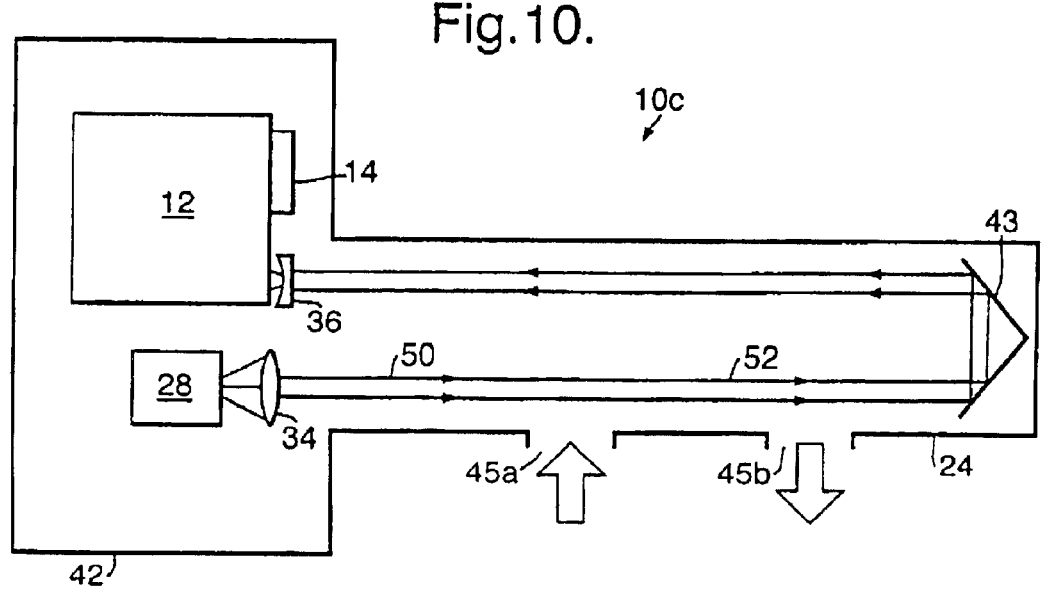
FIG. 10 shows a schematic cross-sectional view of a further modular system for analysing a material.

A system (10c) for analysing a gas is shown in FIG. 10. The system (10c) includes a spectrometer (12), an infra-red detector (14) probe (24), collimating lens (34) diverging lens (36), retroreflector (43), and infra-red source (28), and a chopper (54) (not shown). This system is similar to the previously described embodiments of the invention, but a retroreflector (43) is positioned at the end of the probe instead of ATR element (44), and the probe body (53) has two apertures or windows (45a,b) formed therein so that gas may pass into, and out of, the probe (24). The collimated IR beam interacts with (and is modified by) the gas which is to be analysed, passes to the retroreflector (43) located at the end of the probe, is reflected by retroreflector and passes back along the probe towards the diffraction grating (32). The modified IR beam (52) is then focused and dispersed onto diffraction grating (32) by diverging lens (36) and then to detector (14), as in (he previous embodiments of the invention.

Figure 11:
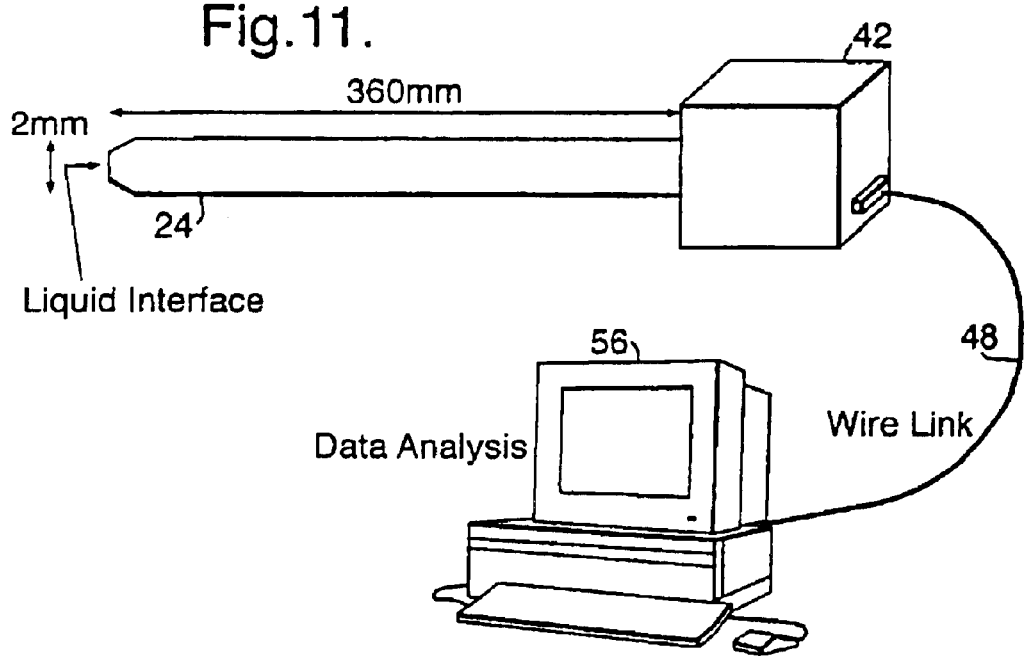
FIG. 11 shows a system for analysing a material.

In the embodiments of the invention, imaging diffraction grating (32) is located within a to spectrometer housing (12). The housing (12) is used to align and keep in position the incoming fiber connection (18) (if a fiber optic connection is used), the detector (14) and the grating (32). The housing (12) is made of a material which is substantially opaque to infra-red radiation in order that stray radiation does not cause spurious/inaccurate signals at the detector (14). The detector (14) may be positioned either inside or outside the housing (12). The probe (24) is rigidly connected to system housing (42), which in turn is connected to a computer (36) or microprocessor by means of wire link (48). The complete system (10) is shown in FIG. 11.

Figure 12A:
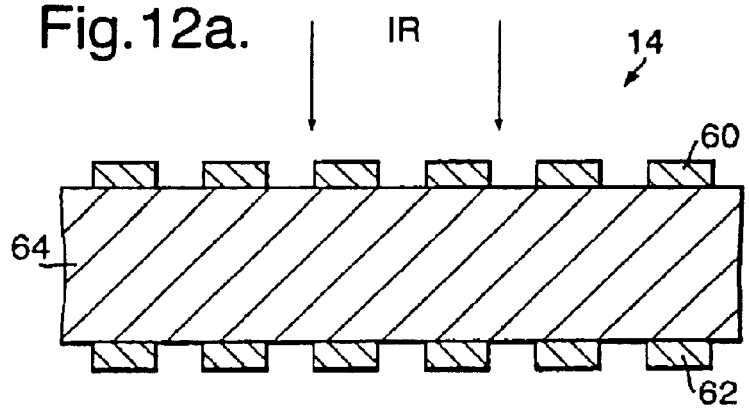
FIGS. 12a and 12b show a schematic cross-sectional view of a first and second pyroelectric detector array.

The structure of the infra-red detector (14) will now be described. The infra-red radiation detector is generally rectangular and includes an array of detector elements (electrodes) (62) formed on the lower surface of a very thin (in the region of 1.25 to 2.0 micrometers) layer of pyroelectric copolymer material (64) which is stretched over a rigid silicon frame (80) (not shown), and an array of upper electrodes (60) which are exposed to the infra-red radiation to be detected. The upper electrodes (60) are formed of a metal or alloy having a high sheet resistance so as to provide the detector (14) with good infra-red absorption qualities. Each discrete lower electrode (62) is connected to an associated electronic circuit element. FIG. 12a shows a schematic diagram of a detector (14) having a one-dimensional array of individual detector elements (60,62). The direction of incident infra-red radiation is illustrated by the arrows.

Figure 12B:
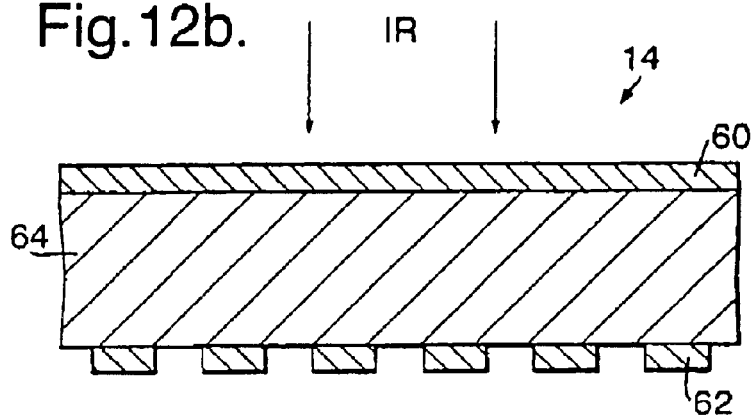

An alternative arrangement of electrodes (60) is shown in FIG. 12b. In this case, the upper electrode (60) is a single common electrode, rather than an array of individual detector electrodes. The lower electrodes (62) are arranged in a one-dimensional array. Two methods of manufacturing this detector (14) will now be described. However, it will be appreciated that these methods can also be used to produce the detector (14) of FIG. 12a. i.e. a detector having an array of individual detector elements formed on both sides of the pyroelectric copolymer material (64).

In the first method of manufacture the detector (14) is made in two main stages: 1) the fabrication of a flexible electrode membrane (78) which supports the electrodes (60,62)and 2) the fabrication of a supporting frame (80) of complementary shape to support the flexible membrane (78).

Figure 13A:
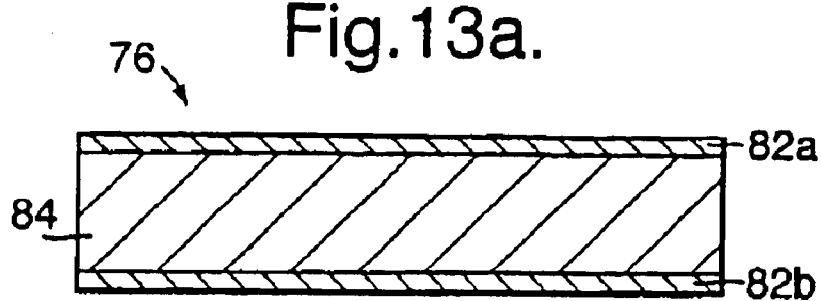
FIGS. 13a to 13e show schematic cross-sectional views of stages in the fabrication of part of the first pyroelectric detector array, according to a first method of fabrication.
Figure 13B:
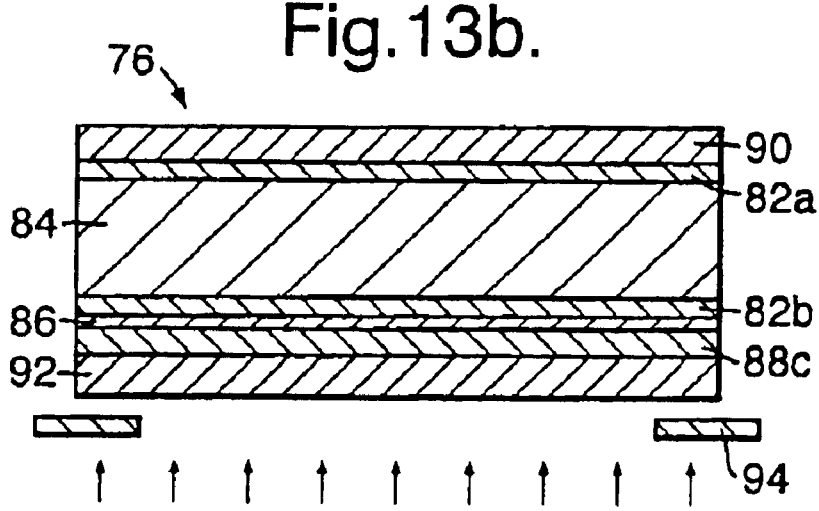

In order to manufacture the supporting frame (80) upper (82a) and lower (82b) layers of silicon nitride are deposited on the upper and lower surfaces of layer (34) of rigid material, as shown in FIG. 13a. In this case a silicon wafer (84) is used. How ever, any rigid material which can be anisotropically etched (eg. a ceramic or a stiff polymer) may be used. A thin nichrome layer (86) is deposited on the exposed surface of the lower silicon nitride layer (82b), followed by a conductive gold layer (88c). The nichrome layer acts as an adhesion layer to enable the gold to adhere to the silicon nitride. The upper silicon nitride lever (82a) is then covered with a protective plastic film (90). A co layer of photoresist (97) is spin-coated onto the old layer (88c), and a mask (94) positioned over the photoresist layer (92). The mask covers the edges of the assembly, but leaves the central portion exposed. The lower surface of the frame assembly is then exposed to ultra-violet radiation, as shown in FIG. 13b.

Figure 13C:
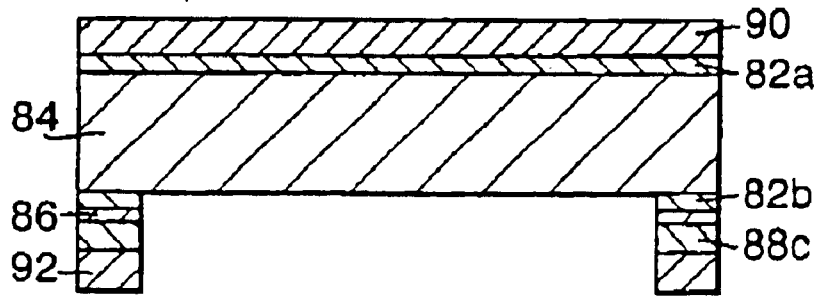

The unwanted portions of photoresist (92) which have been exposed to the ultra-violet radiation are then removed. This leaves a layer of photoresist (92) around the edge of the frame assembly, and an exposed central area of gold (88c). The exposed portion of the gold layer (88c) is removed, along with the adjoining, portions of nichrome (86) and silicon nitride (82b). This leaves an exposed central portion of the lower surface of the silicon wafer (84). This is shown in FIG. 13c.

Figure 13D:
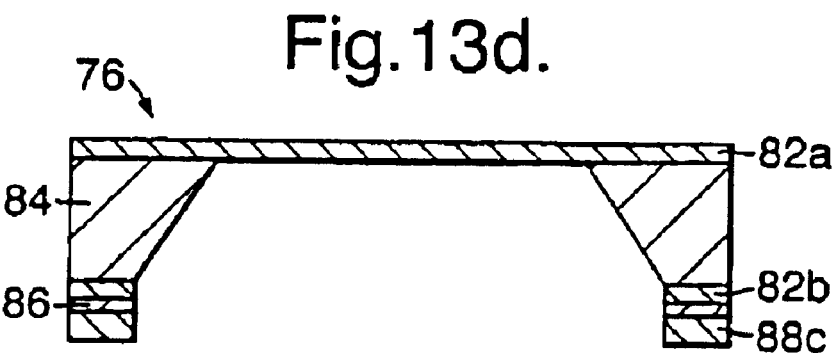
Figure 13E:
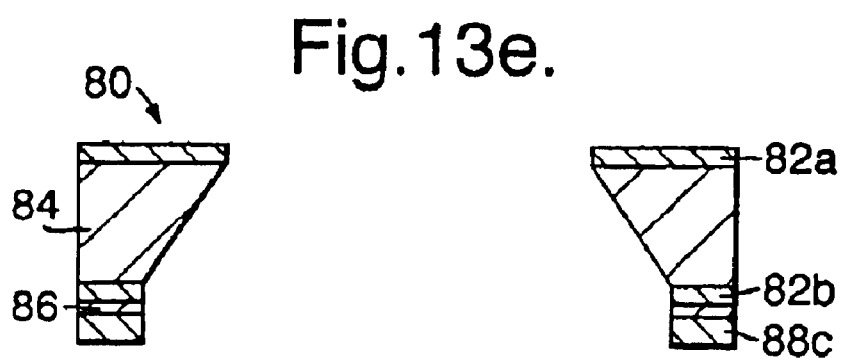
Figure 13F:
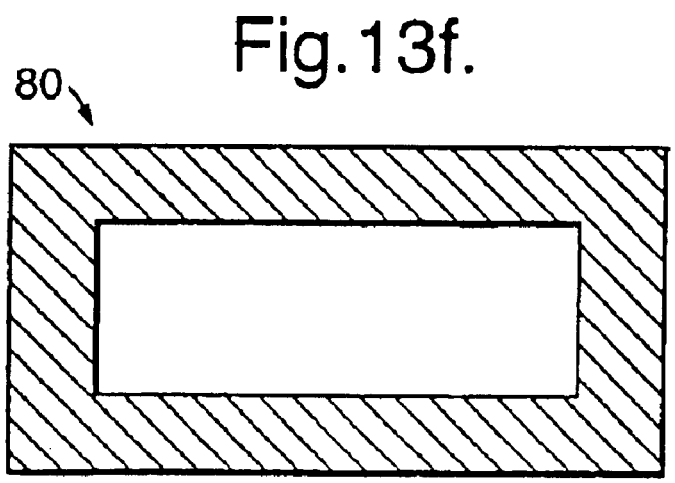
FIG. 13f shows a schematic plan view of part of the first pyroelectric detector array shown in FIGS. 13a to 13e.

The layer of protective plastic film (90) is then removed, along with the lower photoresist (92) portions, to leave the whole of the upper surface of the upper silicon nitride layer (82a) completely exposed. The central portion of silicon wafer (84) is then removed, as shown in FIG. 13d. The central portion of the upper silicon nitride (82a) layer is removed, giving a rectangular supporting frame (SO). A cross-sectional view of the frame (80) is shown in FIG. 13e, and a plan view in FIG. 13f.

The rectangular frame is thus composed of a portion of rigid silicon wafer (84) sandwiched between two silicon nitride layers (82a,b), the lower silicon nitride layer (82b) being in contact with a nichrome layer (86), and the nichrome layer (86) being in contact at its lower surface with a conductive gold layer (83c).

Figure 14A:
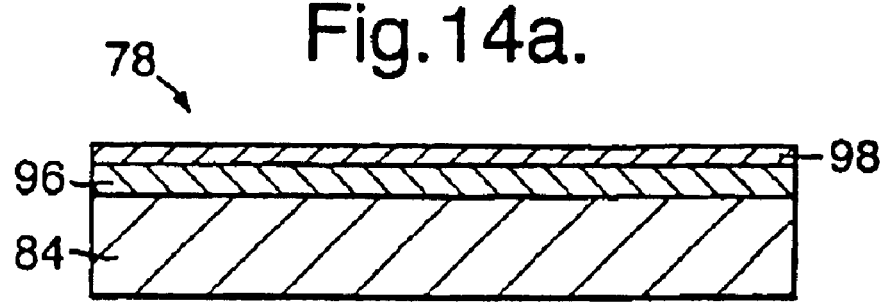
FIGS. 14a to 14e show schematic cross-sectional views of the stages in the fabrication of another part of the first pyroelectric detector array, according to the first method of fabrication.

In order to fabricate the electrode membrane (78) the following steps are carried out. Firstly, a standard grade silicon wafer (84) (or any other suitable rigid material) is spin-coated on its upper surface with a layer of water-soluble polymer, such as PVA (96). This assembly is then baked and a metal layer (98) is deposited on its upper surface, as shown in FIG. 14a. The metal layer (98) can be composed of copper or any other suitable metal such as, for example, nichrome, aluminum, or an alloy. This layer (98) could also be composed of two metals, such as a layer of copper coated with nichrome. The copper layer (90) acts to protect the PVA layer (96) from water during the manufacturing process.

Figure 14B:
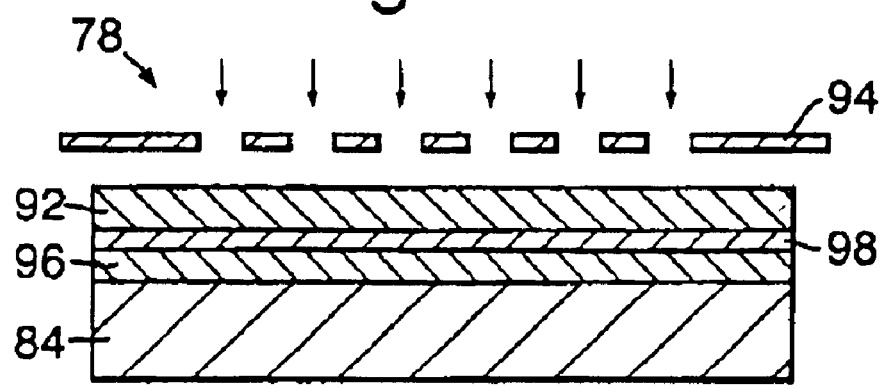
Figure 14C:
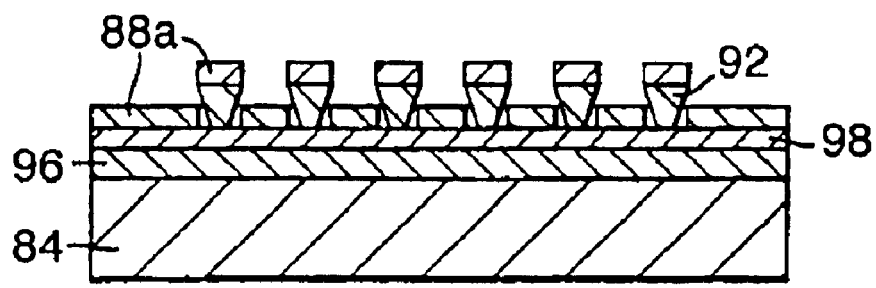

A layer of photoresist (92) is spin-coated onto the metal layer (98), and the assembly exposed to UV radiation through a mask (94), as shown in FIG. 14b. This forms discrete portions of photoresist (92). A conductive layer (88a) of, for example, gold is then deposited on the upper surface of the assembly so as to coat the top of the photoresist portions (92) and the exposed areas of copper (98). The resulting assembly is shown in FIG. 14c.

Figure 14D:
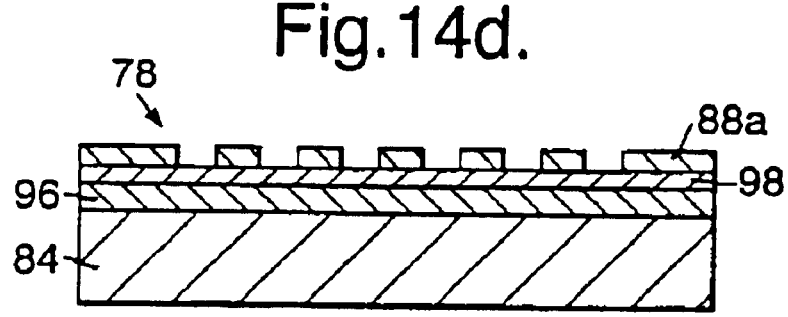
Figure 14E:
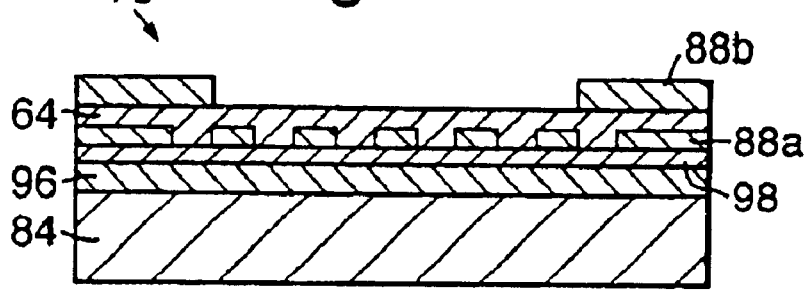

As illustrated by FIG. 14d, the gold-coated photoresist portions (92) are then removed, leaving a patterned layer of gold (88a) with exposed areas of copper (98) therebetween. The gold surface (88a) is roughened in order to Improve adhesion of the next layer. A layer of pyroelectric copolymer (64) is then deposited on the upper surface of the assembly, followed by a further conductive layer (88b) of, for example, gold. The central portions of the upper gold (88b) layer is removed, leaving a central exposed portion of pyroelectric copolymer (64). The resulting structure is shown in FIG. 14e.

Figure 15A:
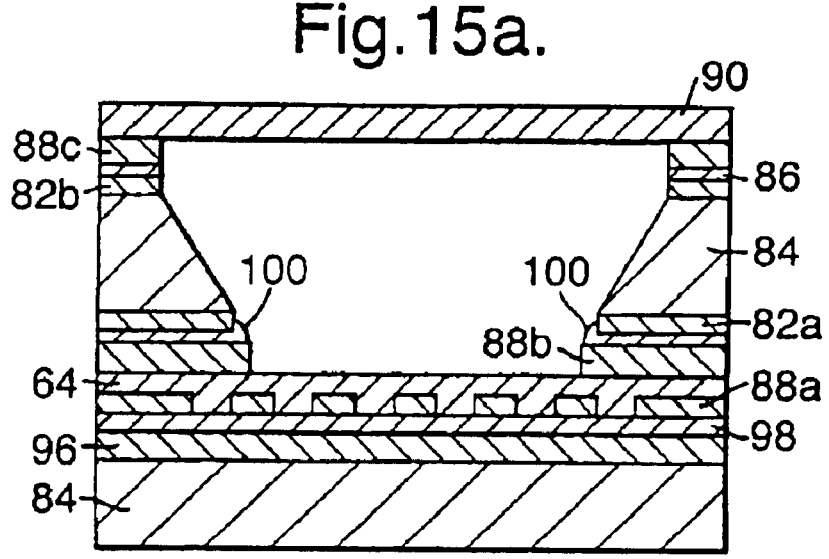
FIG. 15a shows a schematic cross-sectional view of a stage in the fabrication of the first pyroelectric detector array, according to the first method of fabrication.
Figure 15B:
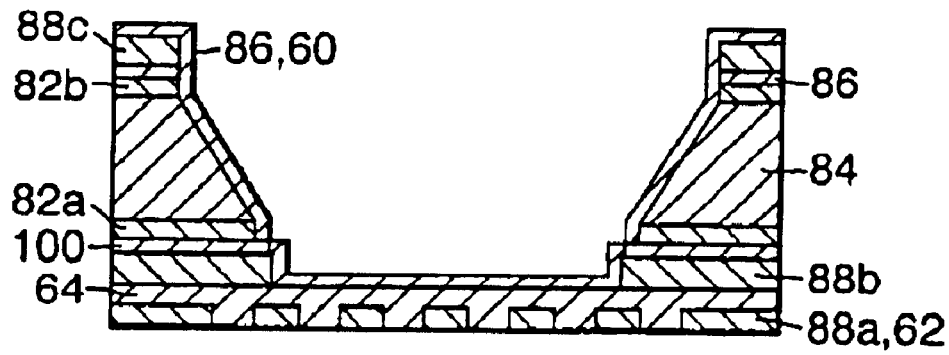
FIG. 15b shows a schematic cross-sectional view of the first pyroelectric detector array, according to the first method of fabrication.

In order to assemble the detector (14), a protective plastic film (90) is placed in contact with gold layer (88c) of the frame (30), and the frame is placed on the electrode assembly (78) so that the upper silicon nitride layer (82a) of the frame is in contact with the upper gold portions (88b) of the electrode assembly. The frame (80) is affixed to the electrode assembly (78) using for example epoxy resin (100), which is subsequently cured by healing the whole structure. The resulting structure is shown in FIG. 15a. The silicon (84). PVA (96) and copper (98) layers are removed from the electrode assembly (78). The protective plastic film (90) is also removed, and the exposed copolymer areas (64) are annealed. The exposed surfaces of the frame (80) and the exposed copolymer area (64) of the membrane (79) are then coated with 377 Ohm/square nichrome to form the upper electrode (60) as shown in FIG. 15b. A voltage is applied between the upper nichrome (60) and lower gold (83a) electrodes in order to polanse the pyroelectric copolymer (64).

In summary, the detector (14) fabricated according to the first method of fabrication comprises a thin pyroelectric copolymer layer (64) in contact with a one-dimensional array of gold electrodes (88a,62) on a first major surface, and a gold layer (88b) (which is of a complementary shape to the frame (80)) on the second opposite major surface. The gold layer (88b) is used for connecting the nichrome electrode (60) to a bond pad. The frame (80) comprises a layer of silicon (84) which supports the electrode membrane (78), sandwiched between a first (82a) and a second (82b) silicon nitride layer. The first silicon nitride layer (82a) of the frame (80) is bonded to the electrode membrane (78). A further gold layer (88c) is attached to the second silicon nitride layer (82b) by way of an adhesion layer (86). The further gold layer (88c) prevents infra-red radiation from passing through the frame structure (80).

In an alternative method or manufacturing the pyroelectric detector array (14), the electrode array can be manufactured using the "back-etching" technique (a one-stage technique), as follows. An assembly is fabricated as previously described with reference to FIGS. 13a to 13c, inclusive. A protective plastic film (90) is then affixed to the lower surface of the structure, so that it is in contact with gold portions (88a). The upper silicon nitride layer (82a) is then coated with 377 Ohm/square nichrome (96b) to form the upper electrode (60), followed by a layer of conductive material (88b) such as gold.

Figure 16A:
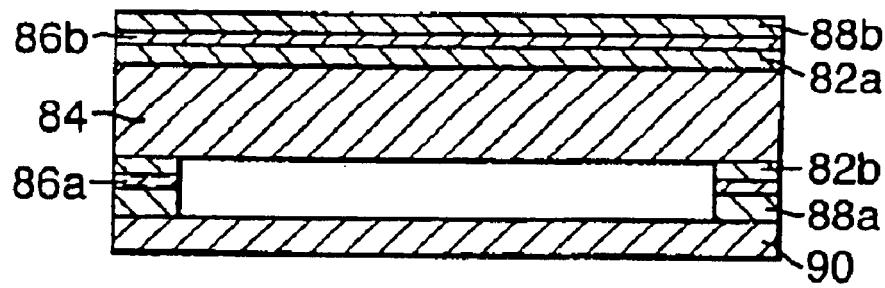
FIGS. 16a to 16d show schematic cross-sectional views of the stages in the fabrication of the first pyroelectric detector array according to a second method of fabrication.
Figure 16B:
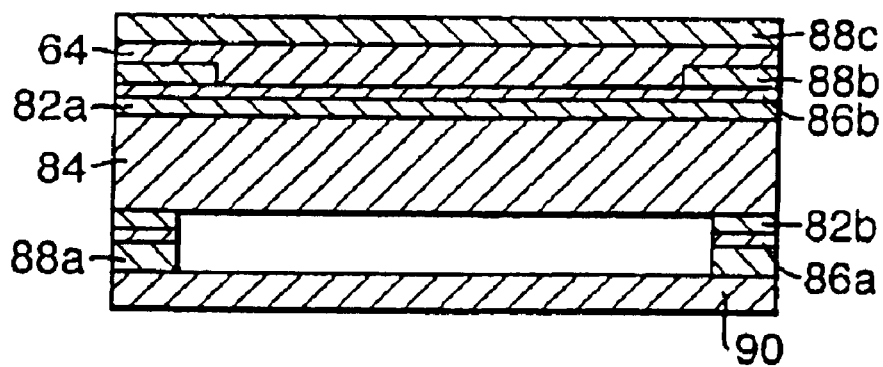

The resulting structure is as shown in FIG. 16a. The central portion of the upper gold layer (88b) is then removed using a suitable technique. The upper surface of the structure is then spin-coated With a pyroelectric copolymer (64). The copolymer layer (64) is coated with a further conductive layer (88c) of, for example, gold, as shown in FIG. 16b.

Figure 16C:
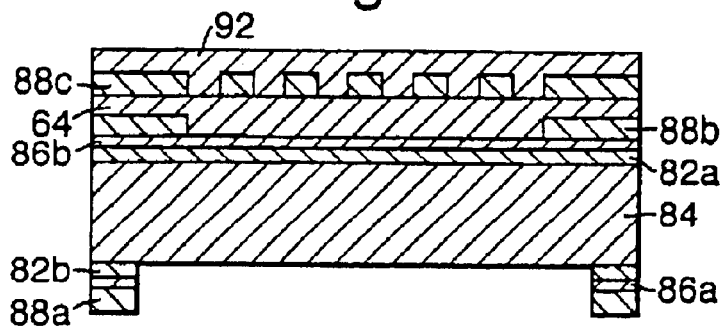
Figure 16D:
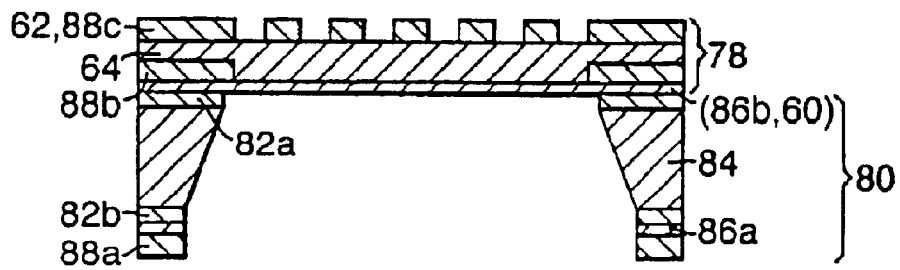

The upper gold layer (88c) of the structure is then photolithographically defined and etched. This leaves a patterned upper surface, which is then covered with a layer of protective photoresist (92). The device is heated and the protective plastic film (90) removed, leaving the structure shown in FIG. 16c. The exposed central portion of the to silicon wafer (84) is then removed, followed by the portion of the silicon nitride layer (82a) adjacent thereto, and also the protective photoresist (92). The resulting structure is shown in FIG. 16d. A voltage is then applied between the gold electrodes (88c,62) and the single nichrome electrode (86b,60) in order to polarise the pyroelectric copolymer (64).

In summary, the detector (14) fabricated according to the second method includes a one-dimensional array of gold electrodes (88c,67) formed on the first major surface of a flexible thin pyroelectric copolymer layer (64), and a common nichrome electrode (86b,60) in contact with the second major surface of the copolymer layer (64). A gold connection layer (88b) (which is of a complementary shape to the supporting layers) is formed in the second major surface of the copolymer layer (64), and is used for connecting the nichrome electrode (86b,60) to a bond pad. The flexible electrode membrane (78) is supported by a frame-shaped layered structure (80). The layered supporting structure is composed of a rigid silicon layer (84) coated on either side with layers of silicon nitride (82a,b). The first silicon nitride layer (32a) is in contact with the nichrome electrode (86b, 60), and the second silicon nitride layer (82b) supports a layer of conductive material (88a) which acts to protect the layered structure from incoming infra-red radiation. The conductive layer (88a) is bonded to the second silicon nitride layer (82b) by way of the adhesion layer (86a).

It will be appreciated that there are many other ways of fabricating the detector (14), including the use of suitable alternative materials, Further suitable pyroelectric detector arrays for use with system (10) are described in European Patents Nos. EP 454398 and EP 345047 (Central Research Laboratories).

During operation of the detector (14), the voltage generated between the electrodes (60,62) is proportional to the rate of change of temperature of the pyroelectric copolymer (64) which in turn depends on the amount of IR radiation absorbed by the copolymer. The amount of infra-red radiation absorbed by the detector (14) can be controlled by careful selection of the material from which electrodes (60,62) are formed. By arranging the front electrode (60) to have a sheet resistance of approximately 377 Ohm/square, and the rear electrodes (62) to act as a reflector, an absorbing quarter-wave cavity is produced. The design of the detector "sandwich" (14) thus optimises the absorption of radiation at a wavelength of four limes the thickness of the pyroelectric copolymer layer (64).

Figure 17:
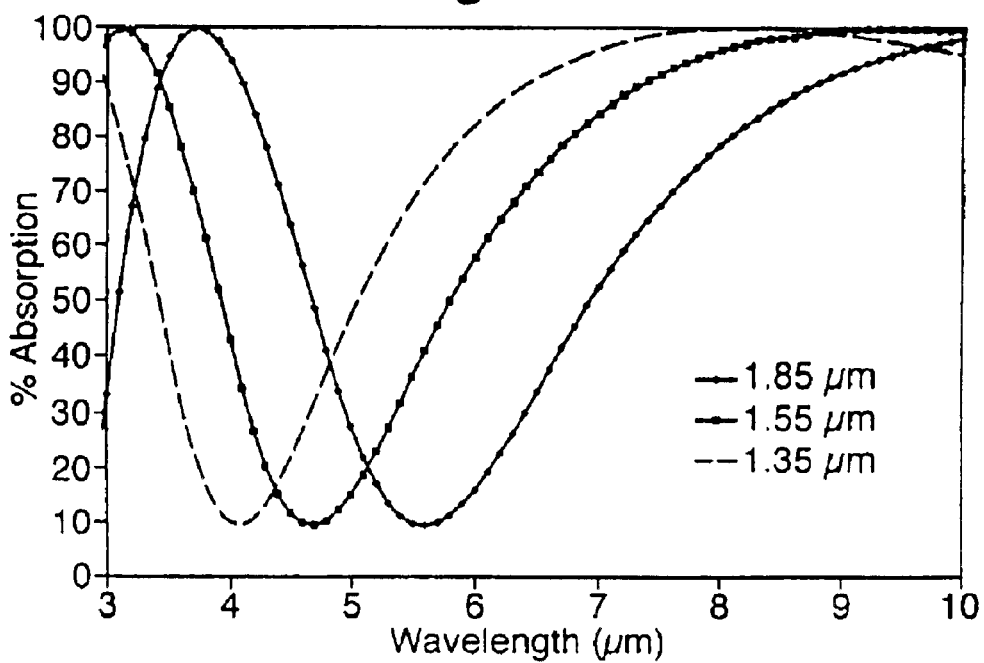
FIG. 17 shows a graph of pyroelectric copolymer absorption as a function of thickness is of a copolymer layer.

In order to optimise the detector (14) to operate over the required band of 5 to 10 micrometers, the thickness of the pyroelectric copolymer layer (64) must be carefully controlled during manufacture. FIG. 17 shows a graph of copolymer absorption as a function of thickness of the copolymer layer (64). The absorption of the pyroelectric layer (64) is also influenced by other factors, such as the amount of IR energy available at each wavelength and the wavelength of interest for analysis.

The array detector (14) contains no electronics itself, and is therefore connected to a custom designed read-out chip. However, electronics may be incorporated into the detector (14). The read-out chip performs the following functions: buffering the detector elements, applying gain, filtering, sampling and multiplexing the output from the detector array. The output signals from the chip is then be fed to a computer or microprocessor for analysis.

Figure 18:
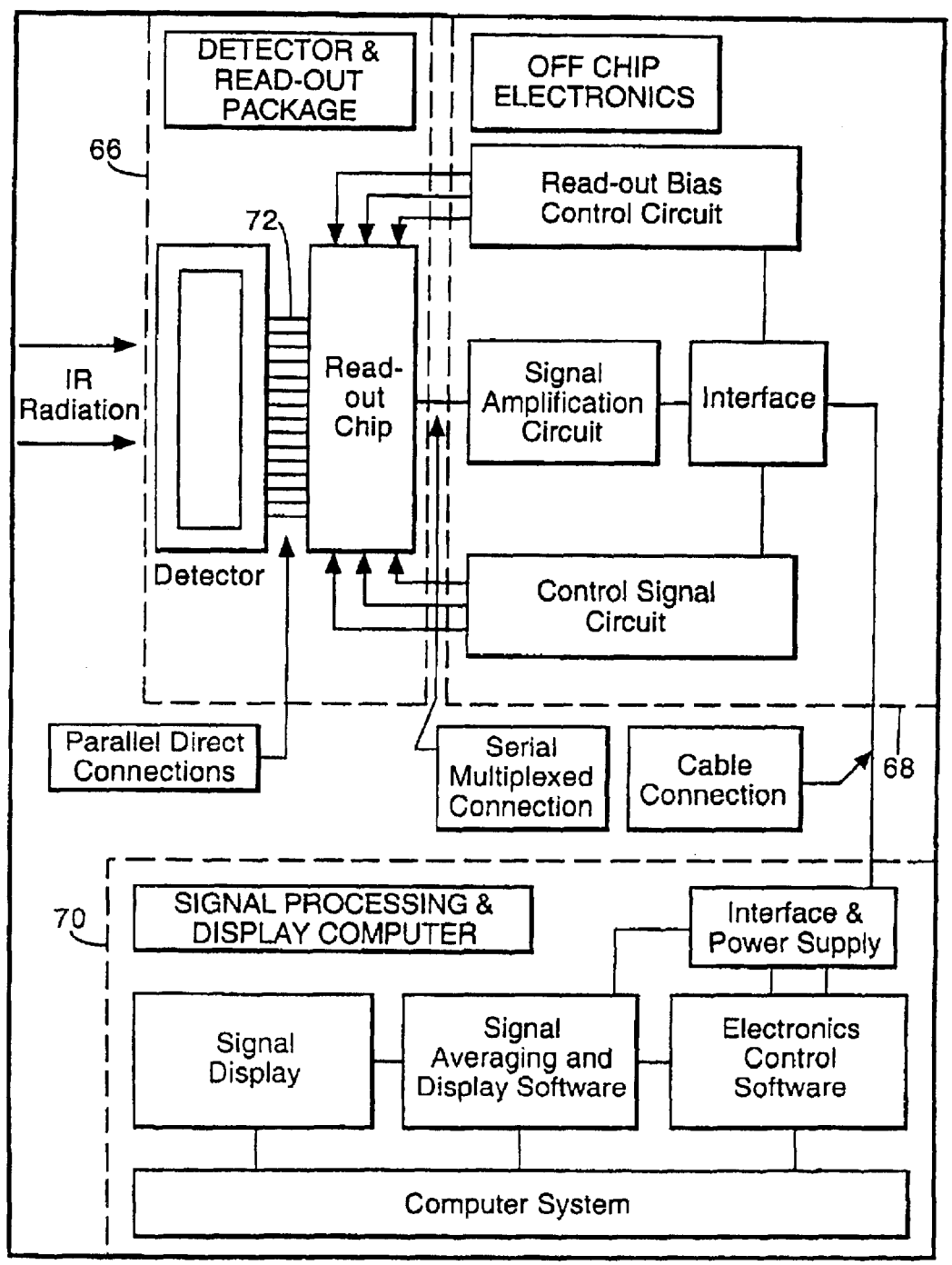
FIG. 18 shows a schematic of the electronics associated with the system.

FIG. 18 shows a diagram of the system electronics. The system is shown as being composed of the following three blocks: 1) the detector and read-out package (66), 2) the off-chip electronics (68), and 3) the signal processor and display (70). The detector and read-out package (66) contains the detector (14) and read-out chip which are interconnected by fine wire bonds (72). The bonds (72) are designed to have the lowest capacitance possible, and are currently formed using short gold wires.

The off-chip electronics package (68) can be realised using any of the current conventional technologies such as surface mount printed circuit boards. Because of its close proximity to the infra-red detector (14), the off-chip electronics (68) must be designed so as to minimise electrical noise. The electronics block (68) performs the functions of controlling the read-out chip, managing the power requirement of the system, and preparing signals for transmission to the next stage of the system. The output from electronics block (63) is a single cable (or wire link) (48) that contains both the signal and the power lines and links to the signal processing and display block (70).

The signal processing and display block (70) is used to process the information obtained to from the detector (14). Signals within this block (70) are in the form of an absorption versus wavelength table. Data in this table can be manipulated as required in order to perform signal averaging signal storage, and transmission to other signal processing applications or to a display.

The invention has been described by way of a number of embodiments, and it will be appreciated that variation may be made to these embodiments without departing from the scope of the invention. For example, the systems described herein may be used for the analysis of liquids, gases, fluidized powders, solutions, mixtures, soils, or gels.

What is claimed is:

1. A method of fabricating a thermal detector, wherein the detector comprises:
    a substantially planar detector membrane, the membrane including a layer of pyroelectric material having first and second major surfaces, the first major surface carrying at least a first electrode, and the second major surface carrying at least a second electrode; and
    supporting means contacting a periphery of the detector membrane for supporting the detector membrane; the method comprising the steps of:
    a) fabricating the substantially planar detector membrane;
    b) fabricating the supporting means for supporting the detector membrane;
    c) affixing the detector membrane to the supporting means; and
    d) forming the first electrode In contact with at least the detector membrane; and wherein the detector membrane Is fabricated according to the following steps:
    a) providing a substantially planar rigid substrate having first and second major surfaces;
    b) depositing a layer of soluble material on the first major surface of the substrate to form a detector assembly;
    c) heating the detector assembly;
    d) depositing a conductive layer on the soluble layer;
    e) depositing a layer of photoresist on the conductive layer;
    f) exposing the detector assembly to ultra-violet radiation through a mask to obtain a patterned photoresist layer;
    g) depositing a layer of conductive material on the patterned photoresist layer and exposed areas of conductive layer;
    h) removing the coated photoresist portions leaving a patterned conductive layer;
    i) depositing layer of pyroelectric material on the patterned conductive layer;
    j) depositing a further conductive layer on the pyroelectric layer; and
    k) removing the central portion of the further conductive layer.

2. A method of fabricating a thermal detector comprising the steps of:
    a) providing a substantially planar rigid substrate having first and second major surfaces;
    b) depositing first and second masking layers on respective first and second major surfaces of the rigid substrate;
    c) depositing an adhesion layer on the second masking layer;
    d) depositing a layer of conductive material on the adhesion layer thereby giving a layered structure;
    e) removing central portions of the conductive layer, the adhesion layer and the second masking layer;
    f) depositing a further conductive layer on the first masking layer to form at least one electrode;
    g) forming a frame of conductive material on the further conductive layer;
    h) depositing a layer of pyroelectric material in contact with the conductive frame and the exposed central portion of the further conductive layer;
    i) forming at least one electrode adjacent the pyroelectric layer; and
    j) removing a central portion of the rigid substrate and the first masking layer thereby forming the detector.

3. A method of fabricating a thermal detector according to claim 2 wherein at least one of the adhesive layer and the further conductive layer includes nichrome.

4. A method of fabricating a thermal detector according to claim 2 wherein the rigid substrate includes silicon.

5. A method of fabricating a thermal detector according to claim 2 wherein the masking layers include silicon nitride.

6. A method of fabricating a thermal detector according to claim 2 wherein the conductive layer includes gold.

* * * * *